United States Patent [19]

Swan et al.

[11] Patent Number: 6,077,698
[45] Date of Patent: Jun. 20, 2000

[54] PHOTOACTIVATABLE CROSS-LINKING AGENTS CONTAINING CHARGED GROUPS FOR WATER SOLUBILITY

[75] Inventors: Dale G. Swan, St. Louis Park; Richard A. Amos, St. Anthony; Terrence P. Everson, Eagan, all of Minn.

[73] Assignee: SurModics, Inc., Eden Prairie, Minn.

[21] Appl. No.: 09/002,457

[22] Filed: Jan. 2, 1998

Related U.S. Application Data

[63] Continuation of application No. 08/552,758, Nov. 3, 1995, Pat. No. 5,714,360.

[51] Int. Cl.[7] .................. C12N 11/00; G01N 33/549; C07K 17/06; C07C 49/76
[52] U.S. Cl. .................. 435/174; 435/177; 435/181; 436/518; 436/532; 530/810; 530/816; 536/1.11; 568/332
[58] Field of Search ................. 435/174, 177, 435/181; 436/518, 532; 530/810, 816; 536/1.11; 568/332

[56] References Cited

U.S. PATENT DOCUMENTS

| | | | |
|---|---|---|---|
| 4,309,453 | 1/1982 | Reiner et al. | 427/54.1 |
| 4,722,906 | 2/1988 | Guire | 436/501 |
| 4,973,493 | 11/1990 | Guire | 427/2 |
| 4,979,959 | 12/1990 | Guire | 623/66 |
| 5,002,582 | 3/1991 | Guire et al. | 623/66 |
| 5,414,075 | 5/1995 | Swan et al. | 568/333 |
| 5,714,360 | 2/1998 | Swan et al. | 435/174 |

OTHER PUBLICATIONS

Menschutkin reaction (Z. Physik. Chem. 5,589 (1890)).
Organic Synthesis Collective vol. IV, 585 (1963).
"Plastics", pp. 462–464, in Concise Encyclopedia of Polymer Science and Engineering, Kroschwitz, ed., John Wiley and Sons, 1990.
Kroschwitz, ed., Polyamines and Polyquaternary Ammonium Salts, Concise Encyclopedia of Polymer Science and Engineering, John Wiley & Sons, 1990, pp. 761–763.

*Primary Examiner*—David M. Naff
*Attorney, Agent, or Firm*—Fredrikson & Byron, P.A.

[57] ABSTRACT

A chemical linking agent is formed of a di- or higher functional photoactivatable compound having at least one group that is charged to improve water solubility, and two or more photoreactive groups (preferably comprising an aryl ketone such as benzophenone) that allow use of the agent in aqueous systems. Charged groups include salts of organic acids such as sulfonate, phosphonate and carboxylate groups, onium groups such as quaternary ammonium, sulfonium and phosphonium groups, and protonated amines. A surface can be coated with a substance such as a synthetic polymer, carbohydrate, protein, lipid, nucleic acid, drug, vitamin, cofactor or dye by forming an aqueous solution of the linking agent and the substance, placing the solution in contact with the surface and activating the photoreactive groups of the linking agent to cross-link the substance to the surface.

9 Claims, No Drawings

PHOTOACTIVATABLE CROSS-LINKING AGENTS CONTAINING CHARGED GROUPS FOR WATER SOLUBILITY

This application is a continuation of application Ser. No. 08/552,758, filed Nov. 3, 1995, now U.S. Pat. No. 5,714,360.

TECHNICAL FIELD

The present invention relates to chemical and/or physical modification of the surface properties of industrially and medically important substrates. In a further aspect, the present invention relates to the various processes useful for modifying the surface properties of bulk materials for specific applications. In this aspect, the present invention relates to such surface modification techniques as plasma deposition, radiation grafting, grafting by photopolymerization, ion implantation, and chemical derivatization.

The present invention further relates to photoactivatable cross-linking agents for use in attaching chemical compounds to other compounds and/or to a substrate surface.

BACKGROUND OF THE INVENTION

The chemical modification of surfaces to achieve desired chemical and/or physical characteristics has been previously described. U.S. Pat. Nos. 4,722,906; 4,973,493; 4,979,959; and 5,002,582 (the disclosures of each of which are incorporated herein by reference), for example, relate to surface modification by the use of latent reactive groups to achieve covalent coupling of reagents such as biomolecules and synthetic polymers to various substrates. The preferred latent reactive group is typically described as a photochemically reactive functional group (i.e., photoreactive group). When exposed to an appropriate energy source, a photoreactive group undergoes a transformation from an inactive state (i.e., ground state) to a reactive intermediate capable of forming covalent bonds with appropriate materials.

Such latent reactive groups can be used to first derivatize a desired compound (e.g., thermochemically), followed by the photochemical attachment of the derivatized compound to a surface. Such a sequential approach is suitable in many situations, but can lack such attributes as speed, versatility, and ease of use, particularly when used with target molecules that are inherently difficult to first derivatize.

Latent reactive groups can also be used to prepare photoactivatable heterobifunctional molecules as linking agents, e.g., having a photoreactive group at one end with a thermochemical attachment group at the other. (See, e.g., the above captioned '582 patent, and Reiner et al.)

Such linking agents can be used for either attaching nonreactive compounds to a surface or for priming a relatively inert surface in order to render it reactive upon exposure to suitable actinic radiation.

U.S. Pat. No. 5,414,075, commonly owned by the assignee of the present application, describes the use of linking agents to prime a surface to provide the surface with photoactivatable groups. This patent describes a restrained, multifunctional reagent useful for priming a support surface, or for simultaneous application with a target molecule to a support.

Reagents such as those described above, including those described in the '075 patent, are generally hydrophobic. As a result, they are of relatively low solubility in aqueous systems, thereby often limiting their usefulness to hydrophobic applications. In turn, linking agents of the prior art are rarely, if ever, coated in compositions that employ water as a primary (e.g., greater than about 50% by vol.) solvent.

On a separate subject, the preparation and use of a class of cationic polyelectrolytes is described, for instance, in "Polyamines and Polyquaternary Ammonium Salts", pp. 761–763, in *Concise Encyclopedia of Polymer Science and Engineering*, Kroschwitz, ed., John Wiley and Sons, 1990, the disclosure of which is incorporated herein by reference. Such polyamines and "polyquats" are described as being useful by virtue of their cationicity in applications involving interactions with anionically charged colloidal particles in aqueous media in nature. They are employed, for instance, in the flocculation of particulate matter from turbid natural waters, as pigment retention aids in the manufacture of paper, and as filtration aids, emulsion breakers, and so on.

Applicants are unaware of the existence of a nonpolymeric photoactivatable linking agent having both improved aqueous solubility and the ability to cross-link or bind otherwise nonreactive molecules to a surface.

SUMMARY OF THE INVENTION

The present invention provides a chemical linking agent comprising a di- or higher functional photoactivatable charged compound. The linking agent of the invention provides at least one group that is charged under the conditions of use in order to provide improved water solubility. The agent further provides two or more photoactivatable groups in order to allow the agent to be used as a cross-linking agent in aqueous systems. In a preferred embodiment, the charge is provided by the inclusion of one or more quaternary ammonium radicals, and the photoreactive groups are provided by two or more radicals of an aryl ketone such as benzophenone.

In a preferred embodiment, the invention provides a linking agent of the general formula:

$$X-Y-X$$

wherein each X, independently, is a radical containing a photoreactive group and Y is a radical containing, inter alia, one or more charged groups. In such an embodiment, the number and/or type of charged group(s) is sufficient to provide the molecule with sufficient aqueous solubility to allow the agent to be used (i.e., applied to a surface and activated) in a solvent system having water as a major component.

In a particularly preferred embodiment, Y contains one or more nitrogen-containing (e.g., quaternary ammonium) groups. More preferably Y contains a linear or heterocyclic radical selected from the group consisting of:

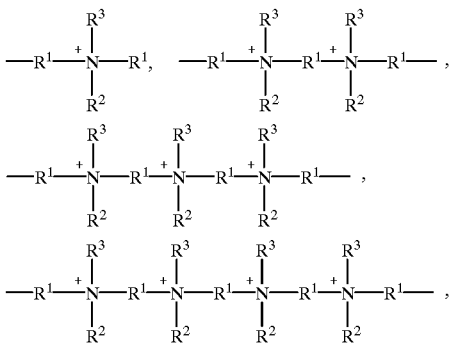

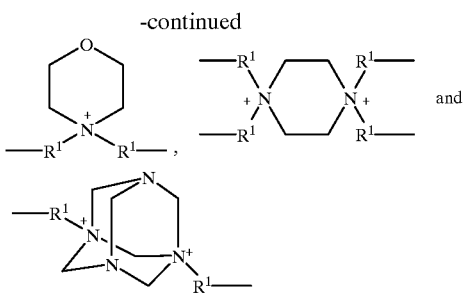

wherein each $R^1$ independently is a radical containing an alkylene, oxyalkylene, cycloalkylene, arylene, or aralkylene group, each $R^2$ independently is a radical containing an alkyl, oxyalkyl, cycloalkyl, aryl, or aralkyl group, and each $R^3$ independently is either a non-bonding pair of electrons, a hydrogen atom, or a radical of the same definition as $R^2$, in which the $R^1$, $R^2$ and $R^3$ groups can contain noninterfering heteroatoms such as O, N, S, P and the like, and /or noninterfering substituents such as halo (e.g., Cl) and the like.

In one preferred embodiment, one or more $R^2$ radicals contains an aralkyl group in the form of a photoactivatable aryl ketone. These groups, in addition to the two photoactivatable groups provided by the above-defined X groups, can be used to provide the "triphoto", "tetraphoto" and higher order photoactivatable groups described herein. The use of three or more total photoreactive groups provides the linking agent with further ability to cross-link the agent to a target molecule and/or to a surface.

In yet another preferred embodiment, the $R^2$ and $R^3$ groups of the above linear radicals can, in effect, be fused (e.g., an $R^2$ and an $R^3$ on a single N atom, or a suitable combination of $R^2/R^3$ groups on adjacent N atoms) in order to form heterocyclic structures other than those exemplified above. The specific choice and relationship between R groups in a linking agent of the present invention is not critical, so long as the linking agent provides two or more photoactivatable groups and retains sufficient water solubility for its intended use.

The term "noninterfering" shall refer to groups, heteroatoms or substituents, the presence of which does not prevent the photoactivatable linking agent from being used for its intended purpose.

The linking agent of the present invention has broad applicability, particularly since it can be used in cross-linking applications where previous linking agents have not been effective. In particular, the presence of one or more charged groups (e.g., salts of organic acids, onium compounds, or protonated amines) provides the agent with enhanced water solubility.

As a result, linking agents of the invention can be used in aqueous systems requiring agents having improved water solubility. This, in turn, provides a cost effective method for the immobilization of inexpensive nonphotoreactive molecules to a surface. Since the linking agents themselves can be prepared from inexpensive starting materials, such as amines and 4-bromomethylbenzophenone (BMBP), the final cost of preparing and using such linking agents can be significantly less than conventional photoreactive agents.

Linking agents of the present invention can be used to simultaneously immobilize (e.g., by cross-linking) otherwise nonreactive molecules to a surface. The agents can also be used to prepare a primed latent reactive surface, which can be used for the later application of a target molecule.

DETAILED DESCRIPTION

As used in the present application the following words and terms shall have the meanings ascribed below:

"water soluble" shall refer to a linking agent of the present invention having sufficient solubility to allow it to be effectively used under aqueous conditions; and "(Mono. di. etc.)photo-(mono. di. etc.)charge" shall be used as a shorthand reference to refer to the total number of photoreactive groups and the total number and type of charged groups in a linking agent of this invention. For instance, "Diphoto-Diquat" shall mean a linking agent of the present invention having two photoreactive groups and two quaternary ammonium groups, examples of which include, but are not limited to, those shown in Formulas II through V of Table I. As other examples, "Triphoto-Triquat" shall mean a linking agent of the present invention having three photoreactive groups and three quaternary ammonium groups (e.g., Formula VI); and "Diphoto-Monosulfonate" shall mean a linking agent having two photoreactive groups and a sulfonate group (e.g., Formula X); and so forth.

In a preferred embodiment, the invention provides a linking agent of the general formula:

$$X—Y—X$$

wherein each X is independently a radical containing a photoreactive group and Y is a radical containing one or more charged groups.

Charge-Containing Radical "Y"

The linking compound of the present invention includes one or more charged groups, and optionally one or more additional photoreactive groups, included in the radical identified in the empirical formula as "Y". A "charged" group, when used in this sense, refers to groups that are present in ionic form, i.e., carry an electrical charge under the conditions (e.g., pH) of use. The charged groups are present, in part, to provide the compound with the desired water solubility.

Preferred Y groups are nonpolymeric, that is, they are not formed by polymerization of any combination of monomers. Nonpolymeric linking agents are preferred since they will tend to have lower molecular mass, which in turn means that they can generally be prepared to have a higher concentration of photoreactive groups per unit mass. In turn, they can generally provide a higher coating density of photoreactive groups than comparable photoreactive polymeric agents (e.g., the photoPVP reagents described in the '582 patent described above).

The type and number of charged groups in a preferred linking agent are sufficient to provide the agent with a water solubility (water at room temperature and optimal pH) of at least about 0.1 mg/ml, and preferably at least about 0.5 mg/ml, and more preferably at least about 1 mg/ml. Given the nature of the surface coating process, linking agent solubility levels of at least about 0.1 mg/ml are generally adequate for providing useful coatings of target molecules on surfaces.

This can be contrasted with linking agents in the art, which are typically considered to be insoluble in water (e.g., have a comparable water solubility in the range of about 0.1 mg/ml or less, and more often about 0.01 mg/ml or less). For this reason, conventional linking agents are typically provided and used in solvent systems in which water is either absent or is provided as a minor (i.e., <50% by volume) component.

Examples of suitable charged groups include, but are not limited to, salts of organic acids (such as sulfonate, phosphonate, and carboxylate groups), onium compounds (such as quaternary ammonium, sulfonium, and phosphonium groups), and protonated amines, as well as combinations thereof. An example of a linking agent employing charged groups other than quaternary ammonium compounds is provided in Formula X of Table I. By reference to the empirical formula provided above, it can be seen that $R^3$ in Formula X would be a lone pair of electrons, in order to provide a tertiary amine group, and $R^2$ would contain a charged sulfonate group in a radical of the formula —$CH_2$—$CH_2$—$SO_3Na$. Sufficient overall charge to render the compound water soluble is provided by the negative charge of the remote sulfonate group.

A preferred charged group for use in preparing linking compounds of the present invention is a quaternary ammonium group. The term "quaternary ammonium", as used herein, refers to organic derivatives of $NH_4^+$ in which the hydrogen atoms are each replaced by radicals, thereby imparting a net positive charge on the radical. The remaining counterion can be provided by any suitable anionic species, e.g., as a chloride, bromide, iodine, or sulfate ion.

Photoreactive "X" Groups

In a preferred embodiment two or more photoreactive groups are provided by the X groups attached to the central Y radical. Upon exposure to a suitable light source, each of the photoreactive groups are subject to activation. The term "photoreactive group", as used herein, refers to a chemical group that responds to an applied external energy source in order to undergo active specie generation, resulting in covalent bonding to an adjacent chemical structure (e.g., an abstractable hydrogen).

Preferred X groups will be sufficiently photoreactive to provide a visual indication of crosslinking in a standardized evaluation of the following type (where additional experimental conditions are provided in the Examples below). A solution containing linking agent of the present invention is used to prepare a coating solution with a water or water/cosolvent system as described herein, the solution having a linking agent concentration between 0.1 to 1 mg/ml. Reagent grade polyvinylpyrrolidone ("PVP", MW approx. 1.5 million daltons), such as that identified as Kollidon 90F ("K-90F") and available from BASF Corporation is added to the coating solution to achieve a final PVP concentration of about 20 mg/ml, and the resulting composition used to coat onto the surface of a polystyrenne slip. The coating composition is then exposed for approximately 4 minutes, in situ, to a suitable light source such as a lamp providing an exposure wavelength of between 250 nm and 450 nm, with an intensity of at least about 1.5 mwatts/sq. cm. at the wavelength range required to promote hydrogen abstraction. The existence of coated PVP (i.e., crosslinked by the linking agent to the polystyrene surface) can be qualitatively determined by staining with Congo Red (Sigma). After extensive washing under a flow of deionized ("DI") water and rubbing, the presence of the bound PVP on the surface is visually verified by staining with a 0.35% solution of Congo Red in DI water.

Preferred groups are sufficiently stable to be stored under conditions in which they retain such properties. See, e.g., U.S. Pat. No. 5,002,582, the disclosure of which is incorporated herein by reference. Latent reactive groups can be chosen that are responsive to various portions of the electromagnetic spectrum, with those responsive to ultraviolet and visible portions of the spectrum (referred to herein as "photoreactive") being particularly preferred.

Photoreactive aryl ketones are preferred, such as acetophenone, benzophenone, anthraquinone, anthrone, and anthrone-like heterocycles (i.e., heterocyclic analogues of anthrone such as those having N, O, or S in the 10-position), or their substituted (e.g., ring substituted) derivatives. The functional groups of such ketones are preferred since they are readily capable of undergoing the activation/inactivation/reactivation cycle described herein. Benzophenone is a particularly preferred photoreactive group, since it is capable of photochemical excitation with the initial formation of an excited singlet state that undergoes intersystem crossing to the triplet state. The excited triplet state can insert into carbon-hydrogen bonds by abstraction of a hydrogen atom (for example, from a support surface or target molecule in the solution and in bonding proximity to the agent), thus creating a radical pair. Subsequent collapse of the radical pair leads to formation of a new carbon—carbon bond. If a reactive bond (e.g., carbon-hydrogen) is not available for bonding, the ultraviolet light-induced excitation of the benzophenone group is reversible and the molecule returns to ground state energy level upon removal of the energy source. Hence, photoreactive aryl ketones are particularly preferred.

Preparation of Linking Agents

Linking agents of the present invention can be prepared using available reagents and chemical conversions within the skill of those in the relevant art. For instance, quaternary ammonium salts can be prepared by the reaction of tertiary amines with alkyl halides using the Menschutkin reaction (Z. Physik. Chem. 5, 589 (1890)). The reaction rates of such conversions can be enhanced by the use of highly nucleophilic tertiary amines, together with alkyl halides having easily displaced halide anions. Typically, the order of reactivity is $I^- > Br > Cl^-$, with primary halides and other highly reactive compounds such as benzylic halides being preferred for the reaction. The synthesis of benzyltrimethylammonium iodide, described in Organic Synthesis Collective Volume IV, 585 (1963), is a representative example of this reaction mechanism.

Di-, tri- or higher order quaternary ammonium compounds of the invention can be prepared, for instance, by reaction of 4-bromomethylbenzophenone ("BMBP") with compounds containing two or more tertiary amine groups. Specific examples of such amines include, but are not limited to, N,N,N',N'-tramethylenediamine, N,N,N',N'-tetramethyl-1,6-hexanediamine, N,N,N',N',N"-pentamethylenediethylenetriamine, and 1,4-dimethylpiperazine.

Table I shows examples of preferred photoactivatable linking agents of the present invention.

TABLE I
| Formula | Compound | Notation | Example |
|---|---|---|---|
| 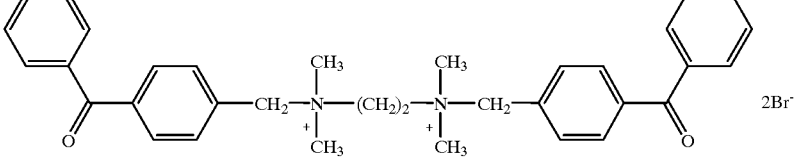 | II | Diphoto Diquat | 2 |
| 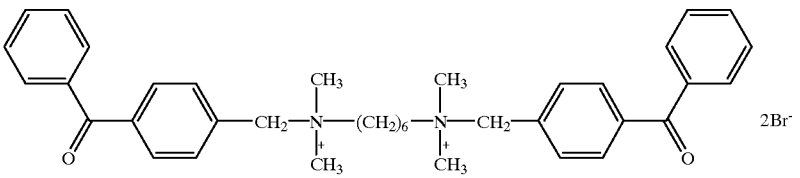 | III | Diphoto Diquat | 3 |
| 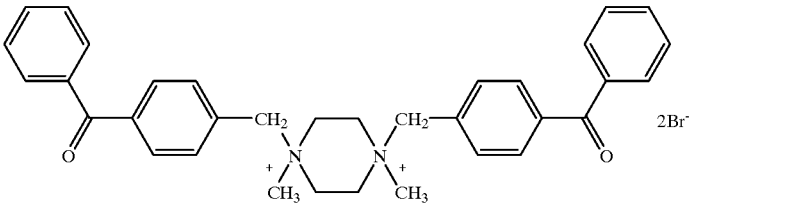 | IV | Diphoto Diquat | 4 |
| 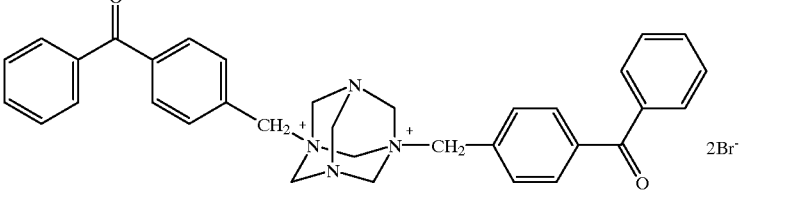 | V | Diphoto Diquat | 5 |
| 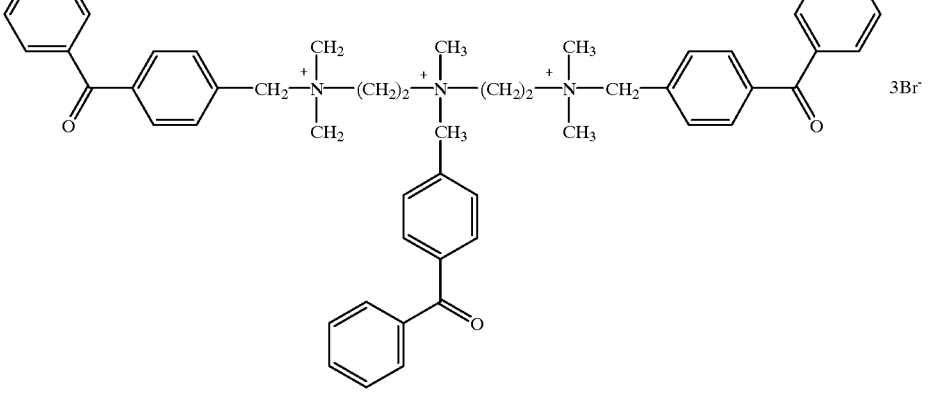 | VI | Triphoto Triquat | 6 |
| 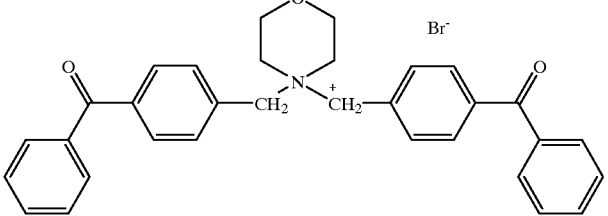 | VII | Diphoto Monoquat | 7 |

TABLE I-continued

| Formula | Compound Notation | Example |
|---|---|---|
| (structure) | VIII Tetraphoto Tetraquat | 8 |
| (structure) | IX Tetraphoto Diquat | 9 |
| (structure) | X Diphoto Monosulfonate | 10 |

Use of Linking Agents

Linking agents can be used in any suitable manner, including by the simultaneous or sequential attachment of a chemical compound to a surface. Linking agents of the present invention can be used to modify any suitable surface. Where the latent reactive group of the agent is a photoreactive group of the preferred type, it is particularly preferred that the surface provide abstractable hydrogen atoms suitable for covalent bonding with the activated group.

Plastics such as polyolefins, polystyrenes, poly(methyl) methacrylates, polyacrylonitriles, poly(vinylacetates), poly (vinyl alcohols), chlorine-containing polymers such as poly (vinyl) chloride, polyoxymethylenes, polycarbonates, polyamides, polyimides, polyurethanes, phenolics, amino-epoxy resins, polyesters, silicones, cellulose-based plastics, and rubber-like plastics can all be used as supports, providing surfaces that can be modified as described herein. See generally, "Plastics", pp. 462–464, in *Concise Encyclopedia of Polymer Science and Engineering*, Kroschwitz, ed., John Wiley and Sons, 1990, the disclosure of which is incorporated herein by reference. In addition, supports such as those formed of pyrolytic carbon and silylated surfaces of glass, ceramic, or metal are suitable for surface modification.

Suitable target molecules for use in the present invention, for attachment to a support surface, encompass a diverse group of substances. Target molecules can be used in either an underivatized form or previously derivatized. Moreover, target molecules can be immobilized singly or in combination with other types of target molecules.

Target molecules can be immobilized to the surface either after (e.g., sequentially) the surface has been primed with linking agent. Preferably, however, target molecules are immobilized during (e.g., simultaneously with) attachment of the present linking agent to the surface.

Typically, target molecules are selected so as to confer particular desired properties to the surface and/or to the device or article bearing the surface. Examples of suitable target molecules, and the surface properties they are typically used to provide, is represented by the following nonlimiting list:

| TARGET MOLECULE | FUNCTIONAL ACTIVITY |
|---|---|
| Synthetic Polymers | |
| Sulfonic acid-substituted polyacrylamide | Lubricity, negatively charged surface, hydrophilicity |
| Polyacrylamide | Lubricity, protein repulsion, hydrophilicity |

-continued

| TARGET MOLECULE | FUNCTIONAL ACTIVITY |
|---|---|
| Polyethylene glycol | Lubricity, cell and protein repulsion, hydrophilicity |
| Polyethyleneimine | Positively charged surface |
| Polylactic acid | Bioerodible surface |
| Polyvinyl alcohol | Lubricity, hydrophilicity |
| Polyvinyl pyrrolidone | Lubricity, hydrophilicity |
| Quaternary amine-substituted polyacrylamide | Lubricity, positively charged surface |
| Silicone | Lubricity, hydrophobicity |
| Conductive polymers (e.g., polyvinylpyridine, polyacetylene, polypyrrole) | Electric conductivity |
| Carbohydrates | |
| Alginic acid | Lubricity, hydrophilicity |
| Cellulose | Lubricity, hydrophilicity, bio-degradable glucose source |
| Chitosan | Positively charged surface, hydrophilicity |
| Glycogen | Hydrophilicity, biodegradable glucose source |
| Heparin | Antithrombogenicity, hydrophilicity, cell attachment |
| Hyaluronic acid | Lubricity, negatively charged surface |
| Pectin | Lubricity, hydrophilicity |
| Mono-, di- saccharides | Hydrophilicity |
| Dextran sulfate | Chromatography media |
| Proteins | |
| Antibodies | Antigen binding |
| Antithrombotic agents (e.g., antithrombin III) | Antithrombogenic surface |
| Albumin | Nonthrombogenic surface |
| Attachment proteins/peptides (e.g. collagen) | Cell attachment |
| Enzymes | Catalytic surfaces |
| Extracellular matrix proteins/peptides | Cell attachment and growth |
| Growth factors, proteins/peptides | Cell growth |
| Hirudin | Antithrombogenic surface |
| Thrombolytic proteins (e.g., streptokinase, plasmin, urokinase) | Thrombolytic activity |
| Lipids | |
| Fatty acids | Hydrophobicity, biocompatibility |
| Mono-, di- and triglycerides | Hydrophobicity, lubricity, bio-degradable fatty acid source |
| Phospholipids | Hydrophobicity, lubricity, bio-degradable fatty acid source |
| Prostaglandins/leukotrienes | Nonthrombogenic surface/immobilized messengers |
| Nucleic Acids | |
| DNA | Substrate for nucleases/affinity binding |
| RNA | Substrate for nucleases/affinity binding |
| Nucleosides, nucleotides | Source of purines, pyrimidines, enzyme cofactors |
| Drugs/vitamins/cofactors | |
| Enzyme cofactors | Immobilized enzymes |
| Heme compounds | Globin bindings/surface oxygenation |
| Drugs | Drug activity |
| Nonpolymeric Materials | |
| Dyes (e.g., azo dyestuffs) | Coloring agents |
| Fluorescent compounds (e.g., fluorescein) | Fluorescence |

Any suitable technique can be used for linking agent attachment to a surface, and such techniques can be selected and optimized for each material, process, or device. The linking agent can be successfully applied to clean material surfaces as listed above by spray, dip, or brush coating of a solution of the reactive linking agent. In a typical simultaneous application, the support intended for coating is first dipped in an aqueous solution of linking agent and target molecule. Suitable aqueous solvents for use in the present invention include at least about 50% water (by volume), and optionally include between about 10% and about 50% of one or more suitable cosolvents such as isopropyl alcohol. The cosolvent typically has little, if any effect on the solubility of the linking agent in the solvent system, and is instead used to reduce the surface tension of the solution in order to promote effective coating of the surface. The coated surface is then exposed to ultraviolet or visible light in order to promote covalent bond formation between the lining agent, target molecule, and material surface, after which the support is washed to remove unbound molecules.

In a typical sequential application, the support is first dipped in an aqueous solution of the linking agent and the linking agent-coated support is then exposed to ultraviolet or visible light in order to promote covalent bond formation at the material surface. After washing to remove any unbound linking agent, a solution containing the target molecule is applied, followed by a second UV illumination which results in attachment of the target molecule to the surface via the linking agent.

When desired, other approaches can be used for surface modification using the linking agent of the present invention. This approach is particularly useful in those situations in which a support is difficult to modify using conventional chemistry, or for situations that require exceptional durability and stability of the target molecule on the surface.

The present invention provides a reagent and method useful for altering the surface properties of a variety of devices of medical, scientific, and industrial importance, using a broad spectrum of suitable target molecules.

The invention will be further described with reference to the following nonlimiting Examples. It will be apparent to those skilled in the art that many changes can be made in the embodiments described without departing from the scope of the present invention. Thus the scope of the present invention should not be limited to the embodiments described in this application, but only by embodiments described by the language of the claims and the equivalents of those embodiments. Unless otherwise indicated, all percentages are by weight.

EXAMPLES

Example 1

Preparation of 4-Bromomethylbenzophenone (Compound I)

4-Methylbenzophenone, 750 g (3.82 moles), was added to a 5 liter Morton flask equipped with an overhead stirrer and dissolved in 2850 ml of benzene. The solution was then heated to reflux, followed by the dropwise addition of 610 g (3.82 moles) of bromine in 330 ml of benzene. The addition rate was approximately 1.5 ml/min and the flask was illuminated with a 90 watt (90 joule/sec) halogen spotlight to initiate the reaction. A timer was used with the lamp to provide a 10% duty cycle (on 5 seconds, off 40 seconds), followed in one hour by a 20% duty cycle (on 10 seconds, off 40 seconds). At the end of the addition, the product was analyzed by gas chromatography and was found to contain 71% of the desired 4-bromomethylbenzophenone, 8% of the dibromo product, and 20% unreacted 4-methylbenzophenone. After cooling, the reaction mixture was washed with 10 g of sodium bisulfite in 100 ml of water, followed by washing with 3×200 ml of water. The product was dried over sodium sulfate and recrystallized twice from 1:3 toluene:hexane. After drying under vacuum, 635 g of 4-bromomethylbenzophenone were isolated, providing a yield of 60%, having a melting point of 112–114° C. Nuclear magnetic resonance ("NMR") analysis ($^1$H NMR (CDCl$_3$)) was consistent with the desired product: aromatic protons 7.20–7.80 (m, 9H) and methylene protons 4.48 (s, 2H). AU chemical shift values are in ppm downfield from a tetramethylsilane internal standard.

Example 2

Preparation of Ethylenebis(4-benzoylbenzyldimethylammonium) Dibromide (Diphoto-Diquat (Compound II)

N,N,N',N'-Tetramethylethylenediamine, 6 g (51.7 mmol), was dissolved in 225 ml of chloroform with stirring. 4-Bromomethylbenzophenone, 29.15 g (106.0 mmol), was added as a solid and the reaction mixture was stirred at room temperature for 72 hours. After this time, the resulting solid was isolated by filtration and the white solid was rinsed with cold chloroform. The residual solvent was removed under vacuum and 34.4 g of solid were isolated for a 99.7% yield, melting point 218–220° C. Analysis on an NMR spectrometer was consistent with the desired product: $^1$H NMR (DMSO-d$_6$) aromatic protons 7.20–7.80 (m, 18H), benzylic methylenes 4.80 (br. s, 4H), amine methylenes 4.15 (br. s, 4H), and methyls 3.15 (br. s, 12H).

Example 3

Preparation of Hexamethylenebis(4-benzoylbenzyldimethylammonium) Dibromide (Diphoto-Diquat (Compound III)

N,N,N',N'-Tetramethyl-1,6-hexanediamine, 1 g (5.80 mmol), was dissolved in 50 ml of chloroform. 4-Bromomethylbenzophenone, 3.35 g (12.18 mmol), was then added as a solid and the resulting solution was stirred at 50° C. for 18 hours. After this time the clear solution was treated with ether. The resulting slurry was allowed to cool to room temperature and the solid allowed to settle. The liquid was decanted and the remaining solid triturated exhaustively with ether. The resulting solid was dried under vacuum to give 4.19 g of solid for a quantitative yield, melting point 208–209° C. Analysis on an NMR spectrometer was consistent with the desired product: $^1$H NMR (DMSO-d$_6$) aromatic protons 7.25–7.90 (m, 18H), benzylic methylenes 4.65 (br. s, 4H), amine methylenes 3.25 (br. s, 4H), methyls 3.00 (br. s, 12H), and methylenes 1.60–2.10 (m, 4H) and 1.20–1.60 (m, 4H).

Example 4

Preparation of 1,4-Bis(4-benzoylbenzyl)-1,4-dimethylpiperazinediium Dibromide (Diphoto-Diquat) (Compound IV)

1,4-Dimethylpiperazine, 1 g (8.76 mmol), was dissolved in 10 ml of chloroform, followed by the addition of 4.94 g (17.96 mmol) of 4-bromomethylbenzophenone. The solid dissolved within 15 minutes with precipitation of the solid product occurring after 30 minutes. The mixture was allowed to stir overnight at room temperature under an argon atmosphere. The product was diluted with ether and the solid was filtered and rinsed with ether. The resulting product was dried under vacuum to give 5.82 g of solid for a quantitative yield, melting point 241–244° C. Analysis on an NMR spectrometer was consistent with the desired product: $^1$H NMR (DMSO-d$_6$) aromatic protons 7.25–7.90 (m, 18H), benzylic methylenes 4.80–5.30 (m, 4H), ring methylenes 2.90–4.40 (m, 8H), and methyls 3.25 (br. s, 6H).

Example 5

Preparation of Bis(4-benzoylbenzyl) hexamethylenetetraminediium Dibromide (Diphoto-Diquat) (Compound V)

Hexamethylenetetramine, 1 g (7.13 mmol), and 4-bromomethylbenzophenone, 4.02 g (14.6 mmol), were dissolved in 100 ml of chloroform at room temperature. This solution was then heated at reflux for 48 hours. After cooling to room temperature, the product was precipitated by the addition of 1 liter of ether and the resulting oily solid was extracted three times with warm ether. Residual solvent was removed under vacuum to give 2.69 g of a white solid for a 54.7% yield, melting point 138–141° C. Analysis on an NMR spectrometer was consistent with the desired product: $^1$H NMR (DMSO-d$_6$) aromatic protons 7.40–7.90 (m, 18H), benzylic methylenes 5.10 (s, 4H), and ring methylenes 5.00 (br. s, 2H), 4.50 (br. s, 8H) and 4.15 (br. s, 2H).

For further purification, a 200 mg sample was loaded on a normal phase flash silica gel column and the nonpolar components were eluted from the column using 10% (v/v) methanol in chloroform. The silica gel bed was then removed and was thoroughly extracted with 10% (v/v) methanol in chloroform to give a purified sample.

Example 6

Preparation of Bis[2-(4-benzoylbenzyldimethylammonio)ethyl]-4-benzoylbenzylmethylammonium Tribromide (Triphoto-Triquat) (Compound VI)

N,N,N',N',N"-Pentamethyldiethylenetriamine, 1 g (5.77 mmol), was dissolved in 20 ml of chloroform with stirring. 4-Bromomethylbenzophenone, 4.84 g (17.60 mmol), was added as a solid and the resulting solution was stirred at 50° C. for 48 hours. After cooling, the solution was treated with ether and the resulting solid was allowed to settle. The liquid was decanted and the remaining solid triturated with ether. The resulting oily solid was dried under vacuum for two hours. The resulting solid weighed 5.08 g for an 88.1% yield, melting point 123–128° C. Analysis on an NMR spectrometer was consistent with the desired product: $^1$H NMR (CDCl$_3$) aromatic protons 7.20–8.10 (m, 27H), benzylic methylenes 5.15 (s, 6H), methylenes 4.05 (br. s, 8H), and methyls 3.35 (br. s, 15H).

Example 7

Preparation of 4,4-Bis(4-benzoylbenzyl) morpholinium Bromide (Diphoto-Monoquat) (Compound VII)

Morpholine, 0.85 g (9.76 mmol), was dissolved in 10 ml of dry tetrahydrofuran ("THF"), followed by the addition of 0.39 g (9.76 mmol) of NaH (60% suspension in oil). The mixture was heated at 50–60° C. for 10 minutes to form the anion, followed by the addition of 2.68 g (9.76 mmol) of 4-bromomethylbenzophenone. The mixture was allowed to stir overnight and then was filtered to remove insolubles, washing the filter cake with 3×10 ml of CHCl$_3$. The solvents were removed under reduced pressure and the product redissolved in 50 ml of CHCl$_3$, followed by washing with 2×30 ml of water. After drying over Na$_2$SO$_4$, evaporation of solvent gave 2.9 g of product, >95% pure by gas chromatographic ("GC") analysis. The analysis on an NMR spectrometer was consistent with the desired product: $^1$H NMR (CDCl$_3$) aromatic protons 7.20–7.80 (m, 9H), methylenes adjacent to oxygen 3.55–3.80 (m, 4H), benzylic methylene 3.50 (s, 2H), and methylenes adjacent to nitrogen 2.30–2.55 (m, 4H).

The above product, 2.4 g (8.07 mmol), was dissolved in 5 ml of CHCl$_3$ with stirring. 4-Bromomethylbenzophenone, 2.22 g (8.07 mmol), was added along with 120 mg (0.80 mmol) of NaI and the mixture was stirred overnight at room temperature. The mixture was filtered and the solid was washed with 3×5 ml of CHCl$_3$ to give 0.95 g of a white solid. The filtrate contained significant amounts of less pure material due to the solubility of the product in organic solvents. $^1$H NMR (DMSO-d$_6$) aromatic protons 7.30–7.85 (m, 18H), benzylic methylenes 4.95 (s, 4H), methylenes adjacent to oxygen 3.90–4.25 (m, 4H), and methylenes adjacent to nitrogen 3.15–3.60 (m, 4H).

Example 8

Preparation of Ethylenebis[(2-(4-benzoylbenzyldimethylammonio)ethyl)-4-benzoylbenzylmethylammonium]Tetrabromide (Tetraphoto-Tetraquat) (Compound VIII)

1,1,4,7,10,10-Hexamethyltriethylenetetramine, 1.0 g (4.34 mmol), is dissolved in 20 ml of chloroform with stirring. 4-Bromomethylbenzophenone, 5.02 g (18.23 mmol), is added as a solid and the mixture is stirred at 50° C. for 48 hours. After cooling, the mixture is treated with ether and the resulting solid is isolated by filtration. The product is rinsed with ether and dried under vacuum.

Example 9

Preparation of 1,1,4,4-Tetrakis(4-benzoylbenzyl) piperazinediium Dibromide (Tetraphoto-Diquat) (Compound IX)

Piperazine, 1 g (11.61 mmol), is dissolved in 20 ml of dry THF, followed by the addition of 0.929 g (23.22 mmol) of NaH (60% suspension in oil). The mixture is warmed at 50–60° C. for 10–20 minutes to form the anion, followed by the addition of 6.39 g (23.22 mmol) of 4-bromomethylbenzophenone. The mixture is stirred overnight and filtered to remove insolubles. After evaporation under reduced pressure, the product is redissolved in 50 ml of CHCl$_3$ and washed with 2×30 ml of water. The product is dried over Na$_2$SO$_4$ and isolated by filtration and evaporation.

The above product is then dissolved in 10 ml of CHCl$_3$, followed by the addition of 6.39 g (23.22 mmol) of 4-bromomethylbenzophenone. NaI, 120 mg (0.80 mmol), is added as a catalyst and the mixture is stirred until the starting materials are consumed. The product is isolated by precipitation with ether and the resulting solid is rinsed with ether and dried under vacuum.

Example 10

Preparation of N,N-Bis[2-(4-benzoylbenzyloxy) ethyl]-2-aminoethanesulfonic Acid, Sodium Salt (Diphoto-Monosulfonate) (Compound X)

Diethanolamine, 5.43 g (51.7 mmol), was diluted with 60 ml of CH$_2$Cl$_2$, followed by the addition of 5.20 g (51.5 mmol) of triethylamine and 11.3 g (51.7 mmol) of di-t-butyl dicarbonate at room temperature. After complete reaction as indicated by GC analysis, volatiles were removed under reduced pressure and the residue was dissolved in 45 ml of CHCl$_3$. The organic was extracted successively with 2×45 ml of 1 N NaOH, 45 ml of 0.1 N NaOH, and 45 ml of 0.01 N NaOH. Each aqueous extract was then back-extracted with 3 ×45 ml of CHCl$_3$. The combined organic extracts were purified on a silica gel flash chromatography column using ethyl acetate to give 6.74 g of t-BOC protected amine as a viscous oil, a 63% yield. The analysis on an NMR spectrometer was consistent with the desired product: $^1$H NMR (CDCl$_3$) hydroxyl protons and methylenes adjacent to oxygen 3.50–3.90 (m, 6H), methylenes adjacent to nitrogen 3.25–3.50 (m, 4H), and t-butyl protons 1.45 (s, 9H).

The t-BOC protected amine, 6.7 g (32.6 mmol), was diluted with 50 ml of dry THF, followed by the addition of 19.72 g (71.72 mmol) of 4-bromomethylbenzophenone, 83 mg (0.55 mmol) of sodium iodide, and 1.75 g (5.43 mmol) of tetra-n-butylammonium bromide. 3.1 g (71.7 mmol) of sodium hydride (55% suspension in oil) was then added portionwise until approximately 80% of the quantity had been added. The mixture was allowed to stir overnight at room temperature, followed by the addition of the remaining 20% of the sodium hydride. After an additional hour of reaction, the product was diluted with 200 ml of water and the product was extracted with 3×100 ml of CHCl$_3$. The bis-benzophenone t-BOC compound was purified on a silica gel flash chromatography column using 95/5 (v/v) CHCl$_3$/acetonitrile, yielding 15.60 g (81% of theory). The analysis on an NMR spectrometer was consistent with the desired product: $^1$H NMR (CDCl$_3$) aromatic protons 7.10–7.80 (m, 18H), benzylic methylenes 4.55 (s, 4H), remaining methylenes 3.30–3.75 (m, 8H), and t-butyl protons 1.45 (s, 9H).

The bis-benzophenone t-BOC compound, 0.52 g (0.877 mmol), was dissolved in 5 ml of ethyl acetate plus 2.5 ml of concentrated HCl and the mixture was stirred 30 minutes at room temperature. The pH was then adjusted to approximately 14 by the addition of 10 N NaOH and the desired product was extracted with 4×10 ml of CHCl$_3$. After drying over sodium sulfate, evaporation of solvent gave the secondary amine product which was used without purification. The analysis on an NMR spectrometer was consistent with the desired product: $^1$H NMR (CDCl$_3$) aromatic protons 7.10–7.80 (m, 18H), benzylic methylenes 4.55 (s, 4H), methylenes adjacent to oxygen 3.60 (t, 4H), methylenes adjacent to nitrogen 2.85 (t, 4H), and amine proton 2.50 (s, 1H).

The secondary amine from above was diluted with 5 ml of N,N-dimethylformamide, followed by the addition of 0.185 g (0.877 mmol) of 2-bromoethanesulfonic acid, sodium salt. Once the solid was dissolved, 0.040 g (1 mmol) of 60% sodium hydride were added and the mixture was warmed at 60° C. When the reaction was found to proceed slowly, 6.3 mg (0.042 mmol) of sodium iodide were added and the heating was continued for 3 days. The product was diluted with 200 ml of water and the product was extracted with 3×200 ml of CHCl$_3$. The desired sulfonate product was isolated by silica gel flash chromatography using CHCl$_3$/CH$_3$OH/NH$_4$OH 90/10/1 (v/v/v) as solvent to give 150 mg of product for a 27% yield. The analysis on an NMR spectrometer was consistent with the desired product: $^1$H NMR (CDCl$_3$) aromatic protons 7.10–7.80 (m, 18H), benzylic methylenes 4.50 (s, 4H), and remaining methylenes 2.90–4.00 (m, 12H).

Example 11

Surface Modification of Polyethylene (PE) by Application of PVP with Compound II A coating solution was prepared by dissolving PVP ("K90F", BASF Corporation) at 20 mg/ml and Compound II at 1 mg/ml in isopropyl alcohol (IPA)/water (1:1). A high density polyethylene ("HDPE") rod (15 cm (6 in) long) was first wiped with an IPA soaked tissue, after which the rod was plasma pretreated at 300 mtorr in argon at 250 watts for two minutes. The rod was dip-coated in the coating solution by dipping into the solution at 2 cm (0.75 in.)/sec., dwelling for five seconds, and withdrawing at a rate of 0.5 cm (0.19 in.)/sec. After removal of the rod from the coating solution, it was air-dried for 10 minutes. The rod was suspended midway between opposed ELC 4000 lamps (40 cm (15.7 in.) apart) containing 400 watt mercury vapor bulbs which put out 1.5 mW /sq. cm from 330–340 nm at the distance of illumination. The rod was rotated and illuminated for three minutes to insure an even cure of the coating.

Extensive washing under a flow of deionized ("DI") water and rubbing the surface between the thumb and forefinger (approx. 30 seconds) indicated a strongly adherent layer of lubricous PVP as compared to an uncoated rod. The presence of the bound PVP on the surface was also verified by staining with a 0.35% solution of Congo Red (Sigma) in DI water.

Example 12

Surface Modification of Polyvinyl chloride (PVC) by Application of PVP with Compound II A PVC urinary catheter (17.8 cm (7.0 in.))×(4.0 outer diameter (0.16 in.)) was coated in the manner described in Example 11.

Again extensive washing under a flow of running DI water and rubbing the surface with fingers (approx. 30 sec.) indicated a strongly adherent lubricous coating of PVP as compared to the uncoated control. Also the presence of the bound PVP on the surface was verified by the evenly stained dark red color produced by staining with a 0.35% solution of Congo Red in DI water.

Example 13

Surface Modification of Polyurethane (PU) by Application of PVP with Compound II A polyurethane ("PU") rod (15 cm (6 in.) long) was coated in the manner described in Example 11, except the rod was not plasma pretreated and it was illuminated wet for four minutes (it should be dry after illumination).

The PU rod was washed extensively in a flow of running DI water and rubbing the surface with fingers (approx. 30 sec.) indicated a strongly adherent layer of lubricous PVP. The presence of the bound PVP on the surface was verified by staining as described in Example 11.

Example 14

Surface Modification of Latex Rubber by Application of PVP with Compound II

A latex rubber catheter (16.5 cm (6.5 in.)×6 mm (0.24 in.) outer diameter) was coated and the presence of the surface bound coating of PVP verified in a manner described in Example 13.

Example 15

Surface Modification of PE by Application of PVP and Heparin with Compound II

A piece of HDPE rod (15 cm (6 in.) long) was washed and pretreated in a manner described in Example 11. The rod was initially coated using the coating solution and method described in Example 11. After the initial coat was cured, the rod was subsequently dip-coated in a solution of PVP ( K90F) at 20 mg/ml, heparin (Celsus Corp.) at 10 mg/ml, and Compound II at 1 mg/ml in IPA/water (40:60 v/v) by dipping the solution at 2 cm (0.75 in.)/sec., dwelling for five seconds, and withdrawing at a rate of 0.5 cm (0.19 in.)/ sec. The wet PE rod was suspended midway between opposed ELC 4000 lamps, rotated and illuminated for four minutes (should be dry after illumination) as described in Example 11.

Rubbing the rod between the thumb and forefinger (approx. 30 seconds) under a flow of DI water indicated a lubricous coating of PVP as compared to uncoated control. Also the presence of the bound heparin on the surface was verified by staining with a 0.1% solution of Toluidine Blue O (Sigma) in DI water.

Example 16

Surface Modification of PVC by Application of PVP and Heparin with Compound II

A PVC urinary catheter (20 cm (8 in.)×4 mm (0.16 in.) outer diameter) was coated and the presence of both PVP and heparin bound on the surface verified as described in Example 15.

Example 17

Surface Modification of PU by Application of PVP and Heparin with Compound II

A PU rod (15 cm (6 in.) long) was coated as described in Example 15 except that no plasma pretreatment was utilized. Evaluation of the rod as described in Example 15 indicated the presence of both PVP and heparin tenaciously bound to the rod surface.

Example 18

Surface Modification of Latex Rubber by Application of PVP and Heparin with Compound II A latex rubber urinary catheter (15 cm (6 in.)×6 mm (0.24 in.)) outer diameter) was coated and evaluated as described in Example 15, except no plasma pretreatment was necessary and the catheter was coated using only a solution of PVP (K90F) at 20 mg/ml, heparin (Celsus Corp.) at 10 mg/ml, and Compound II at 1 mg/ml in IPA/water (40:60 v/v). Evaluation of the latex catheters described in Example 15 indicated the presence of PVP and heparin bound to the surface.

Example 19

Surface Modification of PU by Application of PVP with Compound III

A coating solution was prepared by dissolving PVP (K90F) at 20 mg/ml and Compound III at 1 mg/ml in EPA/water (1:1 v/v). A PU rod (10 cm (3.9 in.) long) was wiped initially with an IPA soaked tissue. The rod was dip-coated in the coating solution by immersing into the solution at 2 cm (0.75 in.)/sec., dwelling for five seconds, and withdrawing at a rate of 1 cm (0.39 in.)/sec., The PU rod was removed from the coating solution and suspended midway between opposed ELC 4000 lamps (40 cm (15.7 in.) apart) containing 400 watt mercury vapor bulbs which put out 1.5 mW/sq. cm from 330–340 nm, at the distance of illumination. The wet rod was rotated and illuminated for three minutes to insure an even cure of the coating.

The surface of the cured rod was rubbed by hand under a flow of DI water for 15 seconds and then stained with 0.35% solution of Congo Red which indicated the presence of PVP on the surface. The rod was again rubbed as previously described, followed by another staining with Congo Red. The coated section of the rod evenly stained dark red and felt lubricious compared to the uncoated control. There was no indication that the coating had rubbed off. A control rod coated with only a 20 mg/ml solution of PVP in EPA/water (1:1 v/v) was not lubricious after rubbing, and did not stain with the Congo Red, indicating that the PVP was not tenaciously bound to the PU surface.

Example 20

Surface Modification of PU by Application of PVP with Compound IV, V, or VI

Polyurethane rods (10 cm (3.9 in.)) were coated as described in Example 19 except, the coating solutions contained 1 mg/ml of Compounds IV, V, or VI. The presence of a lubricious coating using each of the crosslinking agents was verified as indicated in Example 19.

Example 21

Surface Modification of PE by Application of PVP with Compound III, IV, V, or VI HDPE rods (12 cm (4.7 in.)) were coated as described in Example 19 with the same concentrations of PVP and Compounds III, IV, V, or VI, except the rods were plasma pretreated at 300 mtorr in oxygen at 100 watts for three minutes. Evaluation of the surface of the rods by both hand rubbing and Congo Red staining as described in Example 19, for all four linking agents indicated an evenly stained dark red coating which felt lubricious compare to uncoated controls.

Example 22

Surface Modification of HDPE, LDPE, PU, and Nylon with PVO1, PVP, and Compound II or VI Two coating solutions were prepared as follows: Solution #1 contained PVO1/PVP( K90F)/Compound II (10/20/1 mg/ml, respectively) in 30% (v/v) IPA in water. Solution #2 contained PVO1/PVP(K90F)/Compound VI (10/20/1 mg/ml, respectively) in 30% (v/v) IPA in water. PVO1 (PhotoPVP) was prepared by copolymerization of 1-vinyl-2-pyrrolidone and N-(3-aminopropyl)methacrylamide (APMA), followed by photoderivatization of the polymer using 4-benzoylbenzoyl chloride under Schotten-Baumann conditions e.g., a two phase aqueous/organic reaction system.

All four substrates, PU rods and LDPE tubing (31 cm (12.2 in.)), and HDPE rods and nylon tubing (20 cm (7.87 in.)) were wiped with IPA soaked tissues and dip-coated in each of the coating solutions by dipping into the solution at 2 cm (0.75 in.)/sec., dwelling for 30 seconds, and withdrawing at a rate of 0.5 cm (0.19 in.)/sec. The substrates were suspended midway between two opposed ELC 4000 lamps, as previously described (Example 11), and the wet substrates were rotated and illuminated for four minutes to adequately cure the coatings.

The cured substrates were rubbed (10 times) between the thumb and forefinger (approx. 30 sec.) under a flow of DI water, stained with 0.35% solution of Congo Red, re-rubbed (30 times) and restained to demonstrate the presence of bound PVP. The tenacity of the coatings on the substrates was evaluated by coefficient of friction (C.O.F.) using a modified ASTM protocol for tubing. Results indicated that the addition of reagents II and VI agents greatly en h aced the durability of the coatings with only a slight decrease in lubricity as compared to the PVO1/PVP controls.

Example 23

Surface Modification of HDPE, LDPE, PU, and Nylon with PVO1 and Compound II or Compound VI The four different substrates were coated with two different solutions. Solution #1 contained PVO1/Compound II (20/0.5 mg/ml, respectively) in 30% (v/v) IPA in water. Solution #2 consisted of PVO1/Compound VI (20/0.5 mg/ml, respectively) in 30% (v/v) IPA in water. The materials were coated and evaluated as described in Example 22. The surface coatings were more tenacious as compared to PVO1/PVP controls without the linking agents but were also less lubricious than the controls, but well within acceptable ranges.

Example 24

Surface Modification of PU by Sequential Application of Compound II, III, IV, V, or VI and PVP PU rods (10 cm (3.9 in.) were wiped with an IPA soaked tissue. The rods were dip-coated in solutions of Compound II (10 mg/ml), Compound III (10 mg/ml), Compound IV (4 mg/ml), Compound V (10 mg/ml), or Compound VI (10 mg/ml) in IPA/water (1:1 v/v) in the manner described in Example 11. The rods were illuminated for one minute with ELC 4000 lamps as previously described (Example 11) and rotated to insure an even cure of the coating. The rods were then dip-coated into a solution of PVP (20 mg/ml) in IPA, allowed to air dry, and then illuminated for three minutes as previously described (Example 11).

The cured rods were rubbed between fingers under running DI water (15sec.) and then stained 0.35% Congo Red to demonstrate the presence of bound PVP on the surface. All of the photoreagents produced tenacious and lubricious coatings on the PU rods except Compound IV coating which exhibited a decrease in the tenacity and lubricity of the PVP coating.

Example 25

Surface Modification of HDPE by Sequential Application of Compound II, III, IV, V, or VI and PVP Flat pieces of HDPE, 5 cm (1.97 in.)×1.5 cm (0.59 in.)×4mm(0.16 in.) were first wiped with an IPA soaked tissue and then each side was pretreated at 300 mtorr in oxygen at 100 watts for one minute. The pieces were then dipped in solutions of Compounds II, III, IV, V, or VI at concentrations previously reported (Example 24). The flat pieces were then illuminated for one minute as described in Example 11. After curing, the pieces were dip-coated into a solution of PVP (20 mg/ml) in IPA, air-dried, and illuminated for three minutes (see Example 11).

Extensive washing under a flow of DI water and rubbing between the thumb and forefinger (2×15 sec.), followed by staining with 0.35% Congo Red indicated tenacious and lubricious coatings with the use of each of the photoreagents.

Example 26

Modification of PU with PVP and Compound VII

Two coating solutions were prepared as follows: Solution #1 contained PVP(K90F)/Compound VII (17/1 mg/ml, respectively) in 50% (v/v) IPA in water. Solution #2 contained PVP(K90F) (12 mg/ml) in 50% (v/v) IPA in water.

PU rods (16 cm (6.3 in.)) were wiped with IPA soaked tissues and dip-coated in each of the coating solutions by dipping into the solution at 2 cm (0.75in)/sec, dwelling for 30 seconds, and withdrawing at a rate of 0.7 cm (0.27 in.)/sec. Samples of both control rods and those coated with Compound VII were either allowed to air dry for 10 minutes prior to illumination or illuminated wet. The substrates were suspended midway between two opposed ELC 4000 (40 cm (15.7 in.) apart) as previously described (Example 11). The rods were rotated and illuminated for two minutes ( dry illumination) or four minutes (wet illumination).

Extensive washing of all the rods under a flow of DI water and rubbing the surface between the thumb and forefinger (appprox. 30 seconds) indicated a strongly adherent layer of lubricious PVP using Compound VII as compared to the controls containing only PVP. Also the presence of the bound PVP on the surfaces treated with PVP and Compound VII was verified by the evenly stained dark red color produced by staining with a 0.35% solution of Congo Red in DI water. Rods only coated with adsorbed PVP exhibited no color or a very light pink stain.

Example 27

Modification of PU with PVP and Compound X

A coating solution was prepared by dissolving PVP (K90F) at 20 mg/ml and Compound X at 1 mg/ml in DI water containing 0.5 equivalent of 0.1 N NaOH. A PU rod (18 cm (7.1 in.) long) was first wiped with an IPA soaked tissue and dip-coated in the coating solution by dipping into the solution at 2 cm (0.74 in.)/sec., dwelling for 15 seconds, and withdrawing at a rate of 1 cm (0.38 in.)/sec. The wet PU rod was suspended midway between opposed ELC 4000 lamps, rotated and illuminated for 3 minutes as described in Example 11.

Extensive washing under a flow of DI water and rubbing the surface between the thumb and forefinger (approx. 30 seconds) indicated an adherent layer of lubricious PVP as compared to an uncoated rod. The presence of the bound PVP on the surface was also verified with a 0.35% solution of Congo Red in DI water.

What is claimed is:

1. A photoactivatable chemical linking agent capable, upon activation, of covalent attachment to a surface and/or target molecule, the agent comprising a charged, nonpolymeric di- or higher functional photoactivatable compound comprising two or more photoreactive groups, each capable of being activated to form a covalent bond with the surface or target molecule, and one or more charged groups, wherein the number and/or type of charged group(s) is sufficient to provide the agent with sufficient aqueous solubility to allow the agent to be used in a solvent system having water as the major component and wherein each charged group is independently selected from the group consisting of sulfonate, phosphonate, and carboxylate groups, wherein the photoreactive groups each, independently, comprise an aryl ketone.

2. The linking agent according to claim 1 wherein each aryl ketone is selected from the group consisting of acetophenone, benzophenone, anthraquinone, anthrone, and anthrone-like heterocycles, and their substituted derivatives.

3. A photoactivatable cross-linking agent comprising a compound of the formula:

$$X—Y—X$$

wherein each X, independently, is a radical containing a photoreactive group comprising an aryl ketone and Y is a radical containing one or more charged groups, wherein the number and/or type of charged group(s) is sufficient to provide the agent with sufficient aqueous solubility to allow the agent to be used in a solvent system having water as the major component and wherein each charged group is independently selected from the group consisting of sulfonate, phosphonate, and carboxylate groups.

4. The linking agent according to claim 3 wherein each aryl ketone is selected from the group consisting of acetophenone, benzophenone, anthraquinone, anthrone, and anthrone-like heterocycles, and their substituted derivatives.

5. A photoactivatable cross-linking agent comprising:

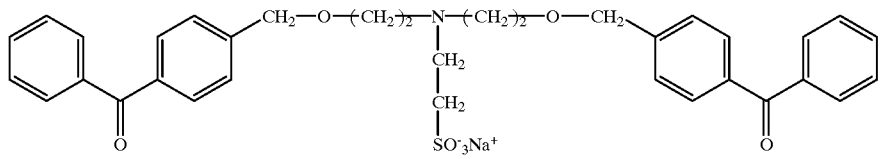

6. A surface bearing a coating comprising a target molecule cross-linked to the surface by the activation of a photoactivatable chemical linking agent, the agent comprising a charged, nonpolymeric di- or higher functional photoactivatable compound, the compound comprising two or more photoreactive groups activated to form covalent bonds with the surface and the target molecule and one or more charged groups, wherein the number and/or type of charged group(s) is sufficient to provide the agent with sufficient aqueous solubility to allow the agent to be used in a solvent system having water as the major component, wherein the photoreactive groups each, independently, comprise an aryl ketone, and wherein the charged groups are each independently selected from the group consisting of sulfonate, phosphonate, and carboxylate groups.

7. The surface according to claim 6 wherein each aryl ketone is selected from the group consisting of acetophenone, benzophenone, anthraquinone, anthrone, and anthrone-like heterocycles, and their substituted derivatives.

8. A method of coating a surface with a target molecule, the method comprising the steps of: a) providing a photoactivatable chemical linking agent capable, upon activation, of covalent attachment to a surface and the target molecule, the agent comprising a charged, nonpolymeric di- or higher functional photoactivatable compound comprising two or more photoreactive groups, the photoreactive groups each, independently, comprising an aryl ketone, the compound comprising one or more charged groups, each charged group being independently selected from the group consisting of sulfonate, phosphonate, and carboxylate groups, and forming a solvent system having water as the major component and comprising the linking agent and a target molecule; b) placing the solvent system in bonding proximity to the surface; and c) activating the photoreactive groups of the linking agent in order to cross-link the target molecule to the surface.

9. The method according to claim 8 wherein each aryl ketone is selected from the group consisting of acetophenone, benzophenone, anthraquinone, anthrone, and anthrone-like heterocycles, and their substituted derivatives.

* * * * *

UNITED STATES PATENT AND TRADEMARK OFFICE
CERTIFICATE OF CORRECTION

PATENT NO. : 6,077,698  
APPLICATION NO. : 09/002457  
DATED : June 20, 2000  
INVENTOR(S) : Swan et al.

Page 1 of 1

It is certified that error appears in the above-identified patent and that said Letters Patent is hereby corrected as shown below:

a. Column 7, replace the chemical structure for Compound VI with:

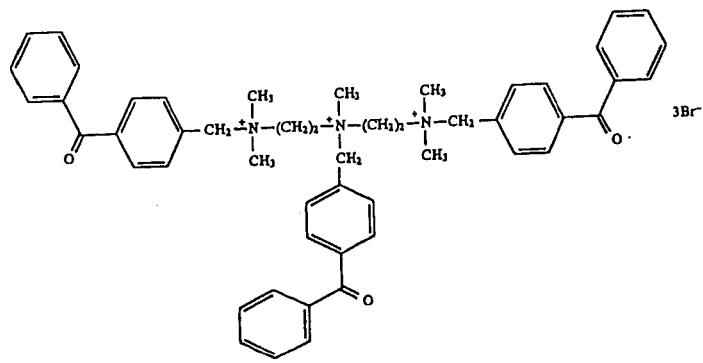

b. Column 9, replace the chemical structure for Compound VIII with:

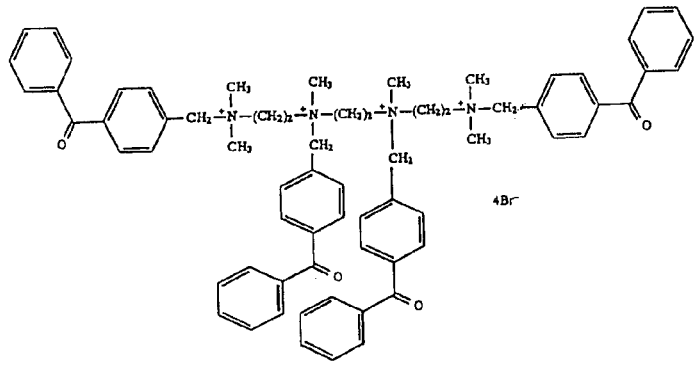

Signed and Sealed this

Nineteenth Day of February, 2008

JON W. DUDAS  
*Director of the United States Patent and Trademark Office*